United States Patent
Peine et al.

(10) Patent No.: US 12,029,510 B2
(45) Date of Patent: Jul. 9, 2024

(54) DETERMINING POSITIONS AND CONDITIONS OF TOOLS OF A ROBOTIC SURGICAL SYSTEM UTILIZING COMPUTER VISION

(71) Applicant: Covidien LP, Mansfield, MA (US)

(72) Inventors: William J. Peine, Ashland, MA (US); Meir Rosenberg, Newton, MA (US); Dwight Meglan, Westwood, MA (US)

(73) Assignee: COVIDIEN LP, Mansfield, MA (US)

( * ) Notice: Subject to any disclaimer, the term of this patent is extended or adjusted under 35 U.S.C. 154(b) by 1036 days.

(21) Appl. No.: 16/960,788

(22) PCT Filed: Jan. 9, 2019

(86) PCT No.: PCT/US2019/012847
§ 371 (c)(1),
(2) Date: Jul. 8, 2020

(87) PCT Pub. No.: WO2019/139949
PCT Pub. Date: Jul. 18, 2019

(65) Prior Publication Data
US 2021/0059775 A1     Mar. 4, 2021

Related U.S. Application Data

(60) Provisional application No. 62/615,590, filed on Jan. 10, 2018.

(51) Int. Cl.
*A61B 34/32*     (2016.01)
*A61B 17/04*     (2006.01)
(Continued)

(52) U.S. Cl.
CPC .......... *A61B 34/32* (2016.02); *A61B 17/0469* (2013.01); *A61B 34/20* (2016.02);
(Continued)

(58) Field of Classification Search
CPC .............. A61B 34/32; A61B 2034/302; A61B 2034/2065
See application file for complete search history.

(56) References Cited

U.S. PATENT DOCUMENTS 6,132,368 A     10/2000   Cooper
6,206,903 B1     3/2001   Ramans
(Continued)

FOREIGN PATENT DOCUMENTS

CN     104582624 A     4/2015
JP     2015527906 A    9/2015
(Continued)

OTHER PUBLICATIONS

Partial Supplementary European Search Report dated Sep. 7, 2021 corresponding to counterpart Patent Application EP 19738088.4.
(Continued)

*Primary Examiner* — Dixomara Vargas
(74) *Attorney, Agent, or Firm* — Carter, DeLuca & Farrell, LLP

(57) ABSTRACT

Robotic Surgical Systems and methods of controlling robotic surgical systems are disclosed herein. One disclosed method includes visually capturing a tool pose of a tool within a surgical site with an imaging device in a fixed frame of reference, determining an arm pose of a linkage supporting the tool from known geometries of the linkage in the fixed frame of reference, and manipulating the linkage to move the tool to a desired tool pose in response to a control signal in the fixed frame of reference.

16 Claims, 6 Drawing Sheets

(51) Int. Cl.
*A61B 34/00* (2016.01)
*A61B 34/20* (2016.01)
*A61B 17/068* (2006.01)
*A61B 17/29* (2006.01)
*A61B 17/295* (2006.01)
*A61B 34/30* (2016.01)

(52) U.S. Cl.
CPC ............ *A61B 34/25* (2016.02); *A61B 17/068* (2013.01); *A61B 17/29* (2013.01); *A61B 17/295* (2013.01); *A61B 2034/2065* (2016.02); *A61B 2034/258* (2016.02); *A61B 2034/301* (2016.02); *A61B 2034/302* (2016.02)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |

(56) References Cited

U.S. PATENT DOCUMENTS

| | | |
|---|---|---|
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,259,290 B2 * | 2/2016 | Jenkins .................. A61B 5/415 |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,360,934 B2 | 6/2016 | Ruiz Morales et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,833,254 B1 * | 12/2017 | Barral ............ A61B 17/320068 |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |

(56) References Cited

U.S. PATENT DOCUMENTS

| | | |
|---|---|---|
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,744,667 B2 * | 9/2023 | Shelton, IV ........ A61B 1/00194 382/128 |
| 2010/0228249 A1 | 9/2010 | Mohr et al. |
| 2010/0312095 A1 | 12/2010 | Jenkins et al. |
| 2013/0030571 A1 | 1/2013 | Ruiz Morales et al. |
| 2013/0169423 A1 | 7/2013 | Iorgulescu et al. |
| 2014/0005684 A1 | 1/2014 | Kim et al. |
| 2014/0323803 A1 | 10/2014 | Hoffman et al. |
| 2016/0008078 A1 * | 1/2016 | Azizian .................. B25J 9/1676 700/255 |
| 2016/0338782 A1 | 11/2016 | Bowling et al. |
| 2016/0354166 A1 | 12/2016 | Popovic et al. |
| 2017/0000574 A1 | 1/2017 | Itkowitz et al. |
| 2017/0172382 A1 | 6/2017 | Nir et al. |
| 2017/0339399 A1 | 11/2017 | Hoffman et al. |
| 2019/0223759 A1 * | 7/2019 | Page ...................... A61B 34/37 |
| 2020/0015925 A1 * | 1/2020 | Scheib ............. A61B 17/00234 |
| 2020/0289219 A1 * | 9/2020 | Denlinger ................ B25J 13/02 |
| 2020/0289222 A1 * | 9/2020 | Denlinger .............. B25J 9/1664 |
| 2021/0196384 A1 * | 7/2021 | Shelton, IV ........... A61B 34/10 |
| 2021/0196424 A1 * | 7/2021 | Shelton, IV ........... A61B 34/25 |
| 2023/0248432 A1 * | 8/2023 | McLoughlin ........ A61B 5/4869 606/11 |

FOREIGN PATENT DOCUMENTS

| | | |
|---|---|---|
| WO | 2016187290 A1 | 11/2016 |
| WO | 2019139944 A1 | 7/2019 |

OTHER PUBLICATIONS

First Examination Report issued in corresponding application IN202017029105 dated Apr. 27, 2022 (5 pages).

Japanese Office Action dated Feb. 24, 2023, issued in corresponding JP Appln. No. 2020538102, 5 pages.

International Search Report mailed May 2, 2019 and Written Opinion completed May 1, 2019 corresponding to counterpart Int'l Patent Application PCT/US2019/012847.

U.S. Appl. No. 62/615,578, filed Jan. 10, 2018, entitled "Surgical Robotic Arms and Pulley Assemblies Thereof".

Chinese Office Action dated Jul. 22, 2023 issued in Chinese Patent Application No. 201980007882.5 (18 pages).

Extended European Search Report dated Nov. 30, 2021 corresponding to counterpart Patent Application EP 19738088.4.

* cited by examiner

DETERMINING POSITIONS AND CONDITIONS OF TOOLS OF A ROBOTIC SURGICAL SYSTEM UTILIZING COMPUTER VISION

CROSS-REFERENCE TO RELATED APPLICATIONS

This application is a National Stage Application of PCT Application Serial No. PCT/US2019/012847 under 35 USC § 371 (a), filed Jan. 9, 2019, which claims benefit of and priority to U.S. Provisional Patent Application Ser. No. 62/615,590 filed Jan. 10, 2018, the disclosures of each of the above-identified applications are hereby incorporated by reference in their entirety.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, etc., in response to movement of input devices by a surgeon viewing images captured by the image capturing device of a surgical site. During a robotic surgical procedure, each of the tools is inserted through an opening, either natural or an incision, into the patient and positioned to manipulate tissue at a surgical site. The openings are placed about the patient's body so that the surgical instruments may be used to cooperatively perform a robotic surgical procedure and the image capturing device may view the surgical site.

During a robotic surgical procedure it is important to accurately know and control the position of the tools within the surgical site. Accordingly, there is a continuing need for systems and methods for detecting and controlling the position of tools within a surgical site during robotic surgical procedures.

SUMMARY

This disclosure relates controlling a surgical robot from visually capturing a tool pose within a surgical site. In disclosed methods, an imaging device captures a tool pose of a tool within a surgical site. The surgical robot then determines an arm pose of a linkage supporting the tool. The surgical robot then manipulates the arm to move the tool to a desired tool pose in response to input from a clinician. Visually determining the tool pose provides improved accuracy and resolution to the position of the tool within the surgical site. The improved accuracy and resolution can be used to complete precision movements and may assist in completing automated actions. Visually determining the tool pose also eliminates discrepancies in kinematic models that are induced by loads and dynamic performance of joints.

In some methods disclosed herein functions of tools are enabled and disabled based on a visually captured tool pose. The function of the tool can be enabled as the end effector of the tool is within an enabled zone of the surgical site. The enabled zone can be determined based on the location of targeted tissue, the size of targeted tissue, the proximity of nontargeted tissue relative to targeted tissue, or the type of function of the tool. The surgical robot can be controlled by a user interface which includes a display. The display shows a graphical representation of the surgical site and can provide visual indicia of the enabled zone and the enabled/disabled status of the function of the tool. For example, the display can have a border that shows one color when the function of the tool is enabled and another color when the function of the tool is disabled. Additionally or alternatively, the display can show the tool in one color when the function of the tool is enabled and show the tool in another color when the function of the tool is disabled. It is contemplated that when the tool is in the enabled zone, the surgical robot can complete automated tasks within the surgical site with the tool. In particular methods, the user interface can track the gaze of the clinician to verify that the clinician's gaze is focused or directed to a representation of the enabled zone on the display before enabling the function of the tool. It is contemplated that by requiring a tool to be within the enabled zone and/or that the clinician's gaze is directed to the enabled zone before activating a function of the tool can increase safety during a robotic surgical procedure by reducing inadvertent or unintended activations of tool functions when the tool is outside of an enabled zone.

In certain methods, a center of view of an imaging device can automatically track a centroid during a surgical procedure. The tracked centroid can be a centroid of a tool, a point between a centroid of a tool and targeted tissue, or a point between centroids of multiple tools. The tracked centroid can be automatically assigned to active tools within the surgical site or can be selectively assigned by the clinician. By automatically tracking a centroid during a surgical procedure, a clinician can concentrate on the procedure without having to focus on moving the imaging device. The method may include receiving the control signal from a user interface of a robotic surgical system.

In an aspect of the present disclosure, a method of controlling a surgical robot includes visually capturing a first tool pose of a first tool within a surgical site in a fixed frame of reference with an imagining device, determining a first arm pose of a first linkage supporting the first tool from known geometries of the first linkage in the fixed frame of reference, and manipulating the first linkage to move the first tool to a desired first tool pose in the fixed frame of reference in response to a first control signal.

In aspects, visually capturing the first tool pose of the first tool in the fixed frame of reference includes defining the fixed frame of reference in a frame defined by the imaging device. Visually capturing the first tool pose of the first tool in the fixed frame of reference may include capturing the first tool pose with both a first lens and a second lens of the imaging device.

In some aspects, visually capturing the first tool pose includes identifying the position of one or more markers on the first tool. Visually capturing the first tool pose may include capturing the position of the one or more markers within an infrared spectrum of light.

In certain aspects, the method includes visually capturing a second tool pose of a second tool within the surgical site in the fixed frame of reference with the imaging device, determining a second arm pose of a second linkage supporting the second tool from known geometries of the second linkage in the fixed frame of reference, and manipulating the second linkage to move the second tool to a desired second tool pose in the fixed frame of reference in response to a second control signal. Determining the first arm pose and determining the second arm pose may occur entirely within the fixed frame of reference.

In another aspect of the present disclosure, a method of controlling a function of a tool of a surgical system including capturing images of a surgical site with an imaging device, determining a distance of the tool within the surgical site relative to targeted tissue, enabling activation of a function of the tool when the tool is within a predetermined distance from the targeted tissue, and activating the function of the tool to manipulate the tool in response to a control signal.

In aspects, the enabling activation of the function of the tool includes providing visual indicia to a clinic engaged with the surgical system that the function is enabled. Providing visual indicia may include changing a color of a border of a display of the surgical system.

In some aspects, the method may include disabling activation of the function of the tool when the tool is beyond the predetermined distance from the targeted tissue. Disabling activation of the function may include providing visual indicia to a clinician engaged with the surgical system that the function is disabled. Providing visual indicia may include changing a color of a border of a display of the surgical system.

In certain aspects, the method may include the surgical system completing an automated task within the surgical site with the tool when the tool is within the predetermined distance from the target tissue. Completing the automated task may include suturing the targeted tissue when the tool is within the predetermined distance from the targeted tissue.

In particular aspects, the method may include verifying that a gaze of a clinician interfacing with the surgical system is directed to an enabled zone on a display of the surgical system before enabling activation of the function of the tool. Activating the function of the tool to manipulate tissue with the tool may include at least one of clamping tissue with the tool, delivering electrosurgical energy to tissue with the tool, stapling tissue with the tool, suturing tissue with the tool, or advancing a cutting edge or knife of the tool through tissue.

In another aspect of the present disclosure, a surgical system includes an imaging device, a tool, and a processing unit. The imaging device is configured to capture images of a surgical site. The tool has a function that is configured to manipulate tissue in response to a control signal. The processing unit is in communication with the imaging device and the tool and is configured to determine a distance of the tool relative to targeted tissue from the captured images and enable activation of the function of the tool when the tool is positioned within a predetermined distance of the targeted tissue.

In aspects, the surgical system includes a display that is configured to provide a representation of the surgical site. The processing unit may be configured to provide a representation of an enablement zone defined by the predetermined distance within the representation of the surgical site. The processing unit may be configured to provide visual indicia on the display when the function of the tool is enabled. The display may be configured to change a color of a border of the display when the function of the tool is enabled.

In some aspects, the surgical system includes a display that is configured to provide a representation of the surgical site. The processing unit may be configured to verify that a gaze of a clinician is directed to the display before enabling activation of the function of the tool. The processing unit may be configured to complete an automated task when the tool is within the predetermined distance of the targeted tissue. The processing unit may be configured to prevent activation of the function of the tool when the tool is positioned beyond the predetermined distance from the targeted tissue.

In another aspect of the present disclosure, a method of manipulating an imaging device includes identifying a tracked centroid within a field of view of the imaging device, manipulating a pose of the imaging device to posing the tracked centroid at a center of the field of view of the imaging device, moving a first tool within the field of view such that the tracked centroid is moved within the field of view of the imaging device, and tracking the tracked centroid as the first tool is moved within the field of view and maintaining the tracked centroid at the center of the field of view of the imaging device.

In aspects, identifying the tracked centroid includes defining the tracked centroid as a first tool centroid of the first tool. Alternatively, identifying the tracked centroid may include defining the tracked centroid as a point between a first tool centroid of the first tool and targeted tissue. The tracked centroid may be a midpoint of a line between the first tool centroid and a centroid of the targeted tissue.

In some aspects, the method includes moving a second tool within the field of view such that the tracked centroid is moved within the field of view of the imaging device. Identifying the tracked centroid may include defining the tracked centroid as appoint between a first tool centroid of the first tool and a second tool centroid of the second tool. The tracked centroid may be a midpoint of a line between the first tool centroid and the second tool centroid. Alternatively, identifying the tracked centroid may include defining the tracked centroid as a point triangulated between a first tool centroid of the first tool, a second tool centroid of the second tool, and targeted tissue.

In certain aspects, manipulating the pose of the imaging device includes moving an arm of a surgical robot supporting the imaging device. Tracking the tracked centroid may include delaying reentering of the field of view of the imaging device until the tracked centroid is misaligned a predetermined distance from the center of the field of view. Tracking the tracked centroid may include limiting a velocity of movement of the field of view of the imaging device.

In another aspect of the present disclosure, a surgical system includes a first tool, an arm, and an imaging device. The first tool is at least partially defines a tracked centroid. The arm is movable within a surgical site. The imaging device is supported on the arm and has a field of view. The imaging device is configured to be manipulated to maintain the tracked centroid at a center of the field of view.

In aspects, the tracked centroid is defined at a first tool centroid of the first tool. Alternatively, the tracked centroid may be defined at a point between a first tool centroid of the first tool and a target within the surgical site.

In some aspects, the surgical system includes a second tool. The tracked centroid may be defined at a point between a first tool centroid of the first tool and a second tool centroid of the second tool. The tracked centroid may be triangulated at a point between a first tool centroid of the first tool, a second tool centroid of the second tool, and a target within the surgical site.

It is envisioned that the methods herein can be implemented in the software of existing robotic surgical systems to improve the efficacy of the existing system. In addition, some of the methods detailed herein can be enhanced with specialized equipment.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
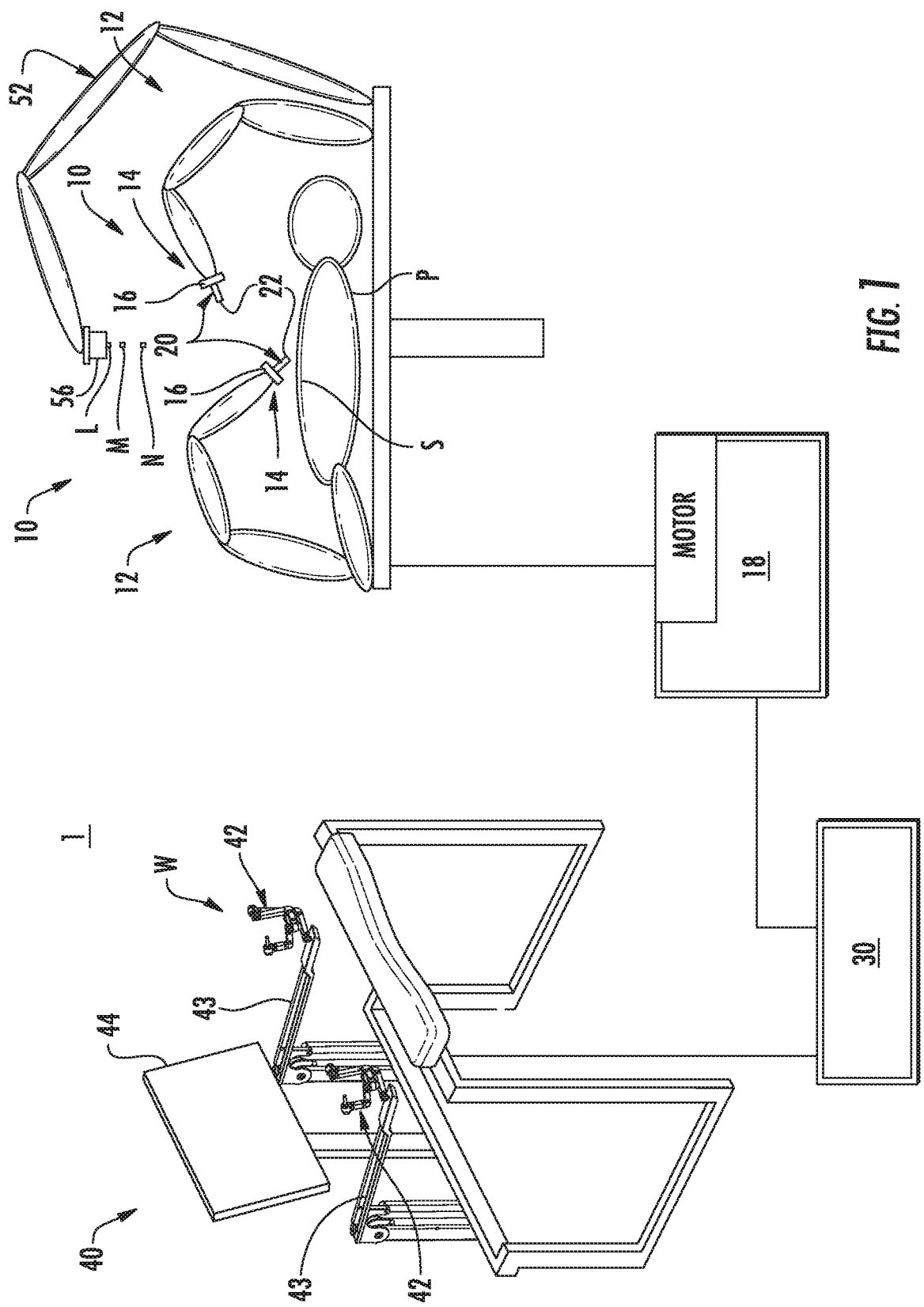
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician or surgical robot arm and the term "distal" refers to the portion of the device or component thereof that is farthest from the clinician or surgical robot arm.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. The arms 12 moveably support a tool 20 having an end effector 22 which is configured to act on tissue. The arms 12 each have an end 14 that supports tool 20. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient, imaging device 56 positioned at a distal end of an imaging linkage or arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which are supported on control arms 43 which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices (not shown) which allow the surgeon to manipulate (e.g., clamp, grasp, fire, open, close, rotate, thrust, slice, etc.) the end effectors 22 of the tools 20 supported at the ends 14 of the arms 12.

Each of the input handles 42 is movable through a predefined workspace to move the ends 14 of the arms 12 within a surgical site "S". The three-dimensional images on the display device 44 are orientated such that movement of the input handle 42 moves the ends 14 of the arms 12 as viewed on the display device 44. It will be appreciated that the orientation of the three-dimensional images on the display device may be mirrored or rotated relative to view from above the patient. In addition, it will be appreciated that the size of the three-dimensional images on the display device 44 may be scaled to be larger or smaller than the actual structures of the surgical site "S" permitting a clinician to have a better view of structures within the surgical site "S". As the input handles 42 are moved, the tools 20, and thus the end effectors 22, are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 2:
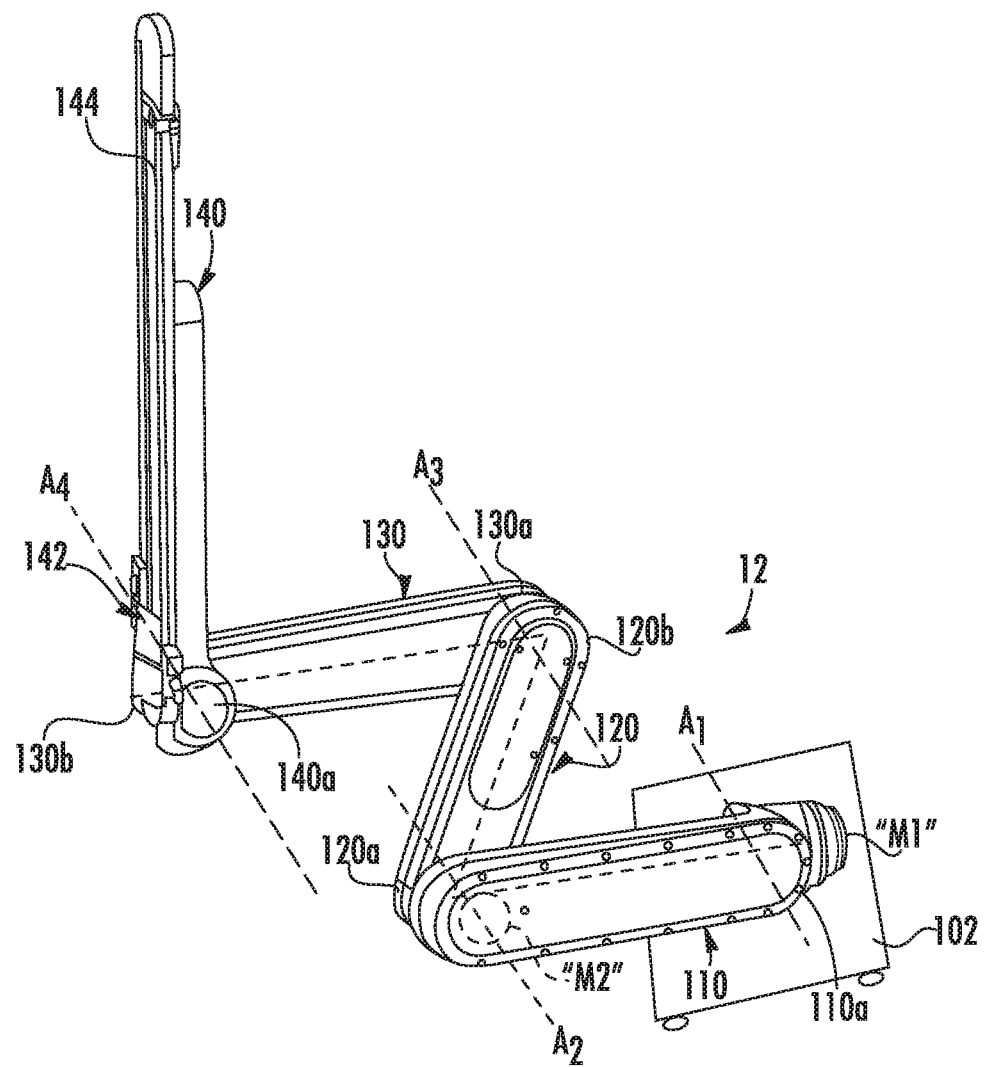
FIG. 2 is a perspective view of a linkage of the robotic system of FIG. 1.

With reference to FIG. 2, the robotic system 10 is configured to support the tool 20 (FIG. 1) thereon and to selectively move the tool 20 in a plurality of orientations relative to a small incision in a patient "P" (FIG. 1) while maintaining the tool 20 within the small incision. The arm 12 includes a plurality of elongate members or links 110, 120, 130, 140 pivotably connected to one another to provide varying degrees of freedom to the arm 12. In particular, the arm 12 includes a first link 110, a second link 120, a third link 130, and a fourth link 140.

The first link 110 has a first end 110a and a second end 110b. The first end 110a is rotatably coupled to a fixed structure. The fixed structure can be a movable cart 102 locked in position, a surgical table, a stanchion, an operating room wall, or other structure present in the operating room. A first motor "M1" is operably coupled to first end 110a to rotate the first link 110 about a first axis of rotation $A_1$ that passes through the first end 110a transverse to a longitudinal axis of the first link 110. The second end 110b of first link 110 has a second motor "M2" operably coupled to a first end of 120a of the second link 120 such that actuation of motor "M2" effects a rotation of the second link 120 relative to first link 110 about a second axis of rotation $A_2$ defined through the second end 110b of first link 110 and a first end 120a of second link 120. It is envisioned the second axis of rotation $A_2$ can be transverse to the longitudinal axis of the first link 110 and a longitudinal axis of the second link 120.

A second end 120b of the second link 120 is operably coupled to the first end 130a of the third link 130 such that the third link 130 rotates relative to the second link 120 about a third axis of rotation $A_3$ that passes through the second end 120b of the second link and the first end 130a of the third link 130. The third axis of rotation $A_3$ is parallel to the second axis of rotation $A_2$. Rotation of the second link 120 about the second axis of rotation $A_2$ affects rotation of the third link 130 about the third axis of rotation $A_3$ such that the first and third links 110, 130 maintain a substantially parallel relationship with one another. For a detailed description of exemplary mechanisms to maintain the substantially parallel relationship between the first and third links, reference may be made to U.S. Provisional Patent Application No. 62/615,578, filed Jan. 10, 2018, and entitled "SURGICAL ROBOTIC ARMS AND PULLEY ASSEMBLIES THEREOF" and PCT Patent Application No. PCT/US2019/12839, filed Jan. 9, 2019, and entitled "SURGICAL ROBOTIC ARMS AND PULLEY ASSEMBLIES THEREOF," the entire contents of which are incorporated herein by reference.

A second end 130b of the third link 130 is operably coupled to a first end 140a of the fourth link 140. The fourth link 140 is rotatable relative to the third link 130 about a fourth axis of rotation $A_4$ that passes through the second end 130b of the third link 130 and the first end 140a of the fourth link 140.

Figure 3:
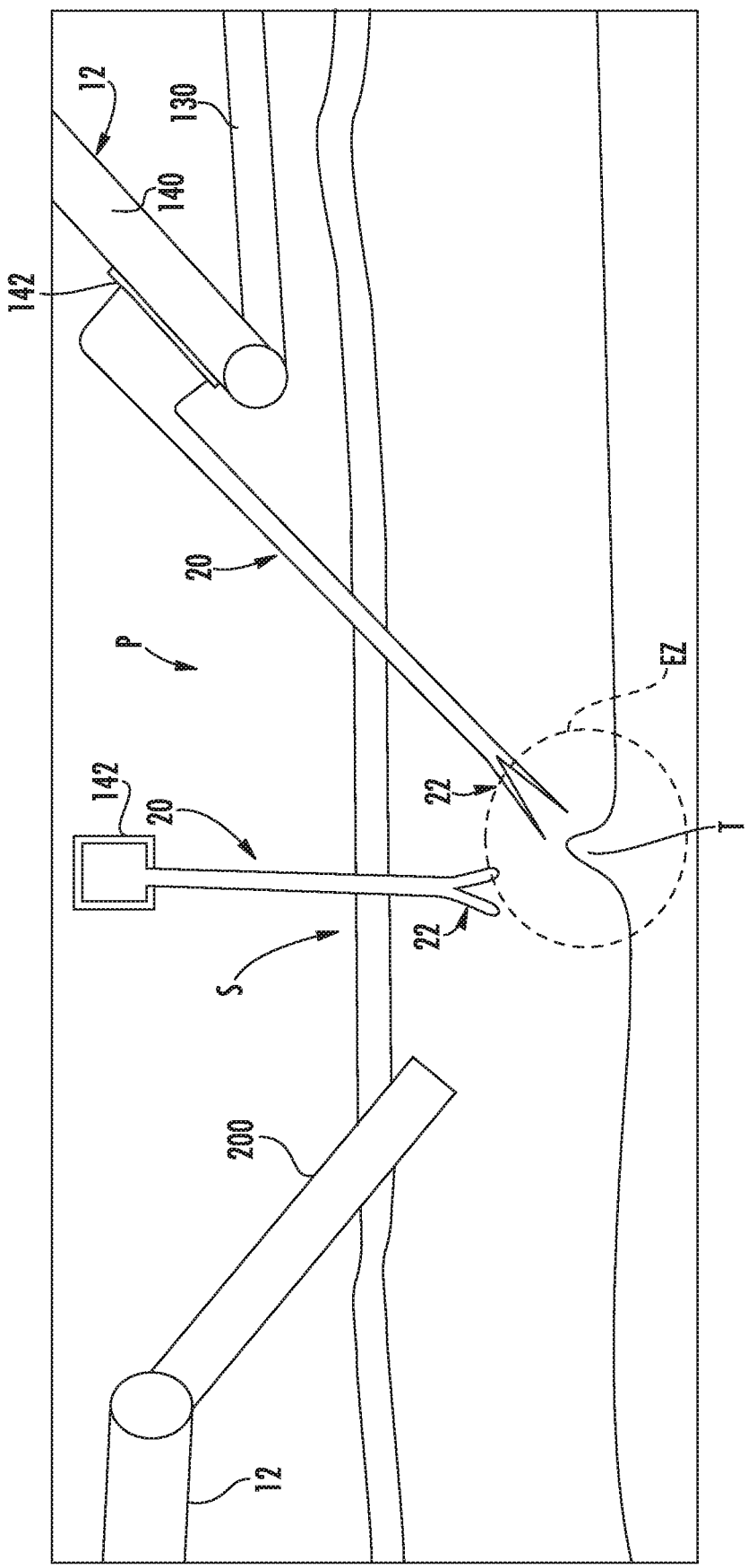
FIG. 3 is a schematic illustration of a surgical site with tools of the robotic system of FIG. 1 inserted therein.

With additional reference to FIG. 3, the fourth link 140 can be in the form of a rail that supports a slider 142. The slider 142 is slidable along an axis parallel to the longitudinal axis of the fourth link 140 and supports the tool 20.

During a surgical procedure, the robotic system 10 receives input commands from the user interface 40 to move the tool 20 such that the end effector 22 is moved to manipulate and/or act on tissue within the surgical site "S". Specifically, the links 110, 120, 130, 140 of the robot arm 12 are rotated relative to one another and the slider 142 is translated to position and orientate the tool 20 within the surgical site "S" in response to the input commands. To control the robot arm 12, the robotic system 10 calculates a desired tool pose of the tool 20 from the input commands, captures a tool pose of the tool 20, and manipulates the robot arm 12 to move the tool 20 to the desired tool pose. From the desired tool pose, the robotic system 10 calculates a required arm pose of the robot arm 12 to achieve the desired tool pose. The robot arm 12 then determines which links 110, 120, 130, 140 to manipulate to reach the required arm pose and thus, the desired tool pose of the tool 20 within the surgical site "S" in response to input captured by the user interface 40 (FIG. 1).

To determine the arm pose of the robot arm 12, the robot system 10 uses an imaging device or endoscope 200 positioned within the surgical site "S" to capture the position and orientation or tool pose of the tool 20 within the surgical site "5". As detailed herein below, the endoscope 200 is described as capturing the tool pose within the surgical site; however, it is contemplated that imaging devices can be used and that each one of the imaging devices can include a single or multiple lenses to capture two or three dimensional images.

The endoscope 200 can be stationary within the surgical site "S", can be manipulated by a clinician within the surgical theater, or can be attached to another robot arm 12 such that the position and orientation of the endoscope 200 can be manipulated during a surgical procedure. The robotic system 10 uses the endoscope 200 to visually capture the tool pose of the tool 20 within the surgical site "S" using known techniques. The tool 20 may include indicia to aid in capturing the tool pose, which may include, but are not limited to, using distinct colors, distinct markings, distinct shapes, or combinations thereof. The tool pose of the tool 20 is captured in a camera frame relative to the endoscope 200 and can be translated to a frame of the surgical site "S", a frame of the tool 20, a frame of the robot arm 12, or any other desired frame of reference. It is envisioned that it may be beneficial to translate the tool pose of the tool 20 to a fixed frame.

From the tool pose of the tool 20, the robotic system 10 can use known kinematics of the robot arm 12 to calculate an arm pose of the robot arm 12 starting from the tool pose of the tool 20 and working towards the first link 110. By calculating the arm pose of the robot arm 12 from tool pose of the tool 20, a solution to move the tool 20 to a desired tool pose within the surgical site "S" accounts for any deformations of the robot arm 12 or the tool 20 when under load. In addition, by calculating the arm pose from the tool pose, it is unnecessary to know the position of the fixed structure (e.g., movable cart 102), to which the first link 110 (FIG. 2) of the arm 12 is coupled, to determine a solution to move the tool 20 to the desired tool pose. In calculating the solution, the robotic system 10 accounts for any possible collisions of the arm 12 with other arms 12, clinicians within the surgical theater, the patient, or other structures within the surgical theater. Further, by calculating the tool pose and/or the arm pose in a common frame, e.g., the camera frame of a single endoscope, the poses of the tools and/or arms can be computed at the same time by using the kinematics of each of the arms, e.g., arm 12, to calculate the locations of the links, e.g., link 110, to estimate possible collisions of the arm 12.

It is contemplated that the robot system 10 can be used to simultaneously capture the tool pose of multiple tools 20 with the endoscope 200. By capturing the tool pose of multiple tools 20, the interaction of the tools 20 and the end effectors 22 of the tools 20 can be controlled with high precision. This high precision control can be used to complete automated tasks; for example, suturing tissue. It is envisioned that by using a single endoscope 200 to capture the tool poses of multiple tools 20, the speed and accuracy of automated tasks can be increased by reducing the need to translate the high precision tool poses from a camera frame to another frame for the duration of the automated task.

It is contemplated that more than one camera and/or endoscope 200 can be used to simultaneously capture the tool pose of the tool 20 within the surgical site "S". It will be appreciated that when multiple cameras are used that it may be beneficial to translate the position and orientation of the tool 20 to a frame other than a frame defined by one of the cameras.

It is contemplated that determining the arm pose from the captured tool pose allows for determining the position of movable carts 102 supporting each of the arms 12 from the captured tool pose and the kinematics of the arms 12. After the surgical procedure is completed, the efficiency of the surgical procedure can be determined and the position of the movable carts 102 recorded. By comparing the position of movable carts 102 during surgical procedures with high efficiency ratings, a guide or recommended locations of the movable carts 102 for a given procedure can be provided to increase the efficiency of future surgical procedures. Increased efficiency of surgical procedures can reduce cost, surgical time, and recovery time while improving surgical outcome.

Figure 4:
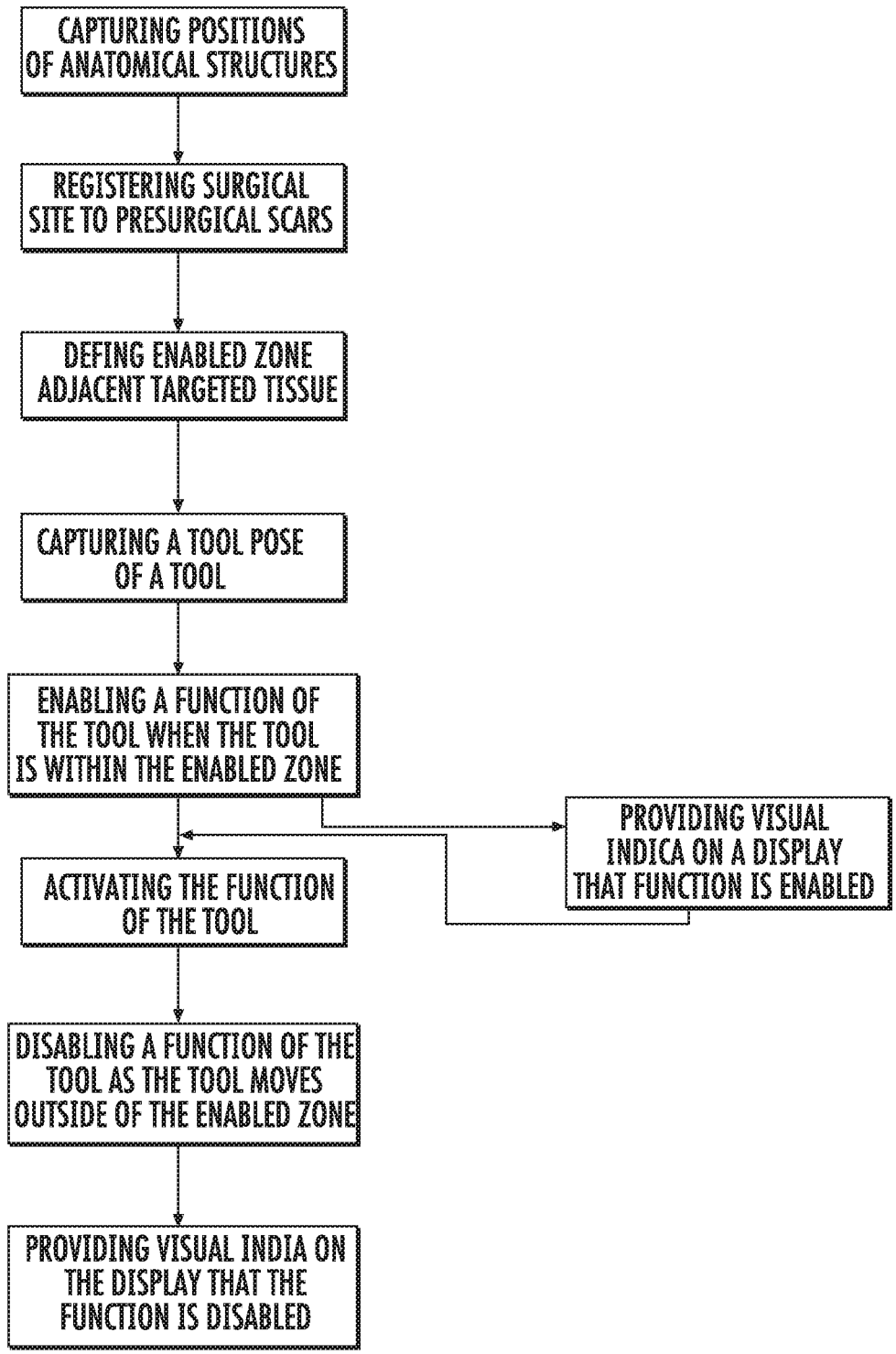
FIG. 4 is a flowchart illustrating a method of enabling a function of a tool of FIG. 3 in response to a tool pose of the tool.

Continuing to refer to FIG. 3 and additionally to FIG. 4, a method of enabling and disabling a function of a tool 20 in response to a captured pose is disclosed in accordance with the present disclosure. During a surgical procedure, the endoscope 200 is used to determine the position of anatomical structures within a surgical site "S". The positions of the anatomical structures can be registered to presurgical scans such that targeted tissue "T" can be identified within the surgical site "S". The targeted tissue "T" can be identified prior to and/or during the surgical procedure and can be identified by the clinician performing the surgery or a clinician remote to the surgical procedure.

With the targeted tissue "T" identified, an enabled zone "EZ" is created about the targeted tissue "T" such that activation of a function of the tool 20 is limited to when the end effector 22 of the tool 20 is within the enabled zone "EZ". By limiting activation of the function of the tool 20 to when the end effector 22 is within the enabled zone "EZ" can prevent inadvertent or unintentional activation of the tool 20.

The enabled zone "EZ" is based on geometric locales within the surgical site "S" adjacent the targeted tissue "T". The size of the enabled zone "EZ" can be based on the function or functions (e.g., clamping, delivery of electrosurgical energy, stapling, suturing, advancement of a knife, etc.) of the tool 20. The enabled zone "EZ" can also be based on the proximity of other anatomical structures to the targeted tissue "T". For example, when other anatomical structures are spaced apart from the targeted tissue "T" the enabled zone "EZ" may be larger than when other anatomical structures are close to or in contact with the targeted tissue "T". The enabled zone "EZ" can be set manually before or during the surgical procedure or can be set automatically based on the function of the tool 20. It is contemplated that for a given surgical procedure, targeted tissue "T" can be in more than one location with the surgical site "S". During such a surgical procedure, the surgical site "S" can include an enabled zone "EZ" about each targeted tissue "T".

Figure 5:
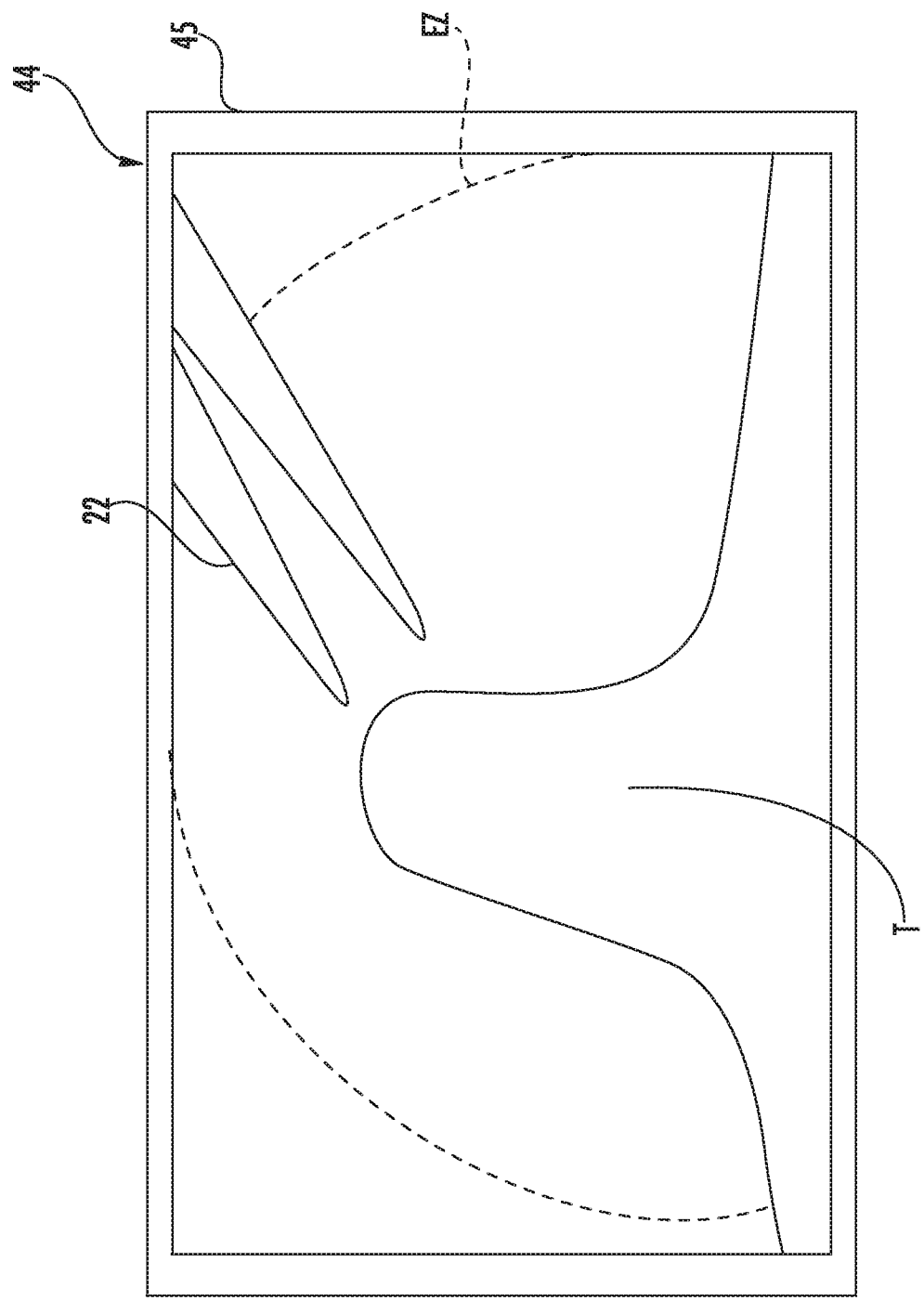
FIG. 5 is a view of a display of the user interface of FIG. 1.

With additional reference to FIG. 5, a graphical representation of the enabled zone "EZ" can be shown on the display 44. The enabled zone "EZ" can be shown as a cloud about the targeted tissue "T" or can be shown clear with the area outside the enabled zone "EZ" appearing as clouded. Additionally or alternatively, the enabled zone "EZ" can be represented by another form of visual delineation on the display 44.

During the surgical procedure, the tool pose of the tool 20, is captured by the camera as detailed above. When the robotic system 10 determines, from the tool pose, that the end effector 22 is outside of the enabled zone "EZ", the robotic system 10 prevents a clinician from activating a function of the tool 20. It is contemplated that the display 44 may also provide a visual indication that the function of the tool 20 is disabled. For example, a border 45 on the display 44 may be red in color, the tool 20 or a portion of the tool 20 (e.g., the end effector 22) may be red in color. Additionally or alternatively, an activation button (not shown) on the input handle 42 (FIG. 1) of the user interface 40 may provide a visual indication (e.g., be backlit in the color red) that the function of the tool 20 is disabled.

As the robotic system 10 determines, from the tool pose, that the end effector 22 enters the enabled zone "EZ", the robotic system 10 enables the function of the tool 20. As the tool 20 enters the enabled zone "EZ", the display 44 may provide a visual indication that the function of the tool 20 is enabled. For example, the border 45 on the display 44 may be green, the tool 20 or a portion of the tool 20 (e.g., the end effector 22) may be green. Additionally or alternatively, an activation button (not shown) on the input handle 42 (FIG. 1) of the user interface 40 may provide a visual indication (e.g., be backlit in green) that the function of the tool 20 is enabled.

It is envisioned that during a surgical procedure where multiple tools 20 are within the surgical site "S". The tools 20 may independently enable a function of the tool 20 based on the position of the end effector 22 of the respective tool relative to the enabled zone "EZ" of the targeted tissue "T". Alternatively, it is contemplated that where multiple tools are within the surgical site "S", that functions of the tools 20 may only be enabled when both end effectors 22 are positioned within the enabled zone "EZ". Limiting enablement of the functions in such a manner may be preferred when the tools 20 cooperate together to act on the targeted tissue "T".

The method may include verifying a gaze of a clinician engaged with the user interface 40 is directed to the enabled zone "EZ" on the display 44 before enabling a function of the tool 20. Specifically, during the surgical procedure, the user interface 40 tracks the gaze of the clinician engaged therewith. As the endoscope 200 determines that the end effector 22 of one of the tools 20 enters the enabled zone "EZ", the user interface 40 verifies that the gaze of the clinician engaged with the user interface 40 is directed to a portion of the display 44 including a representation of the targeted tissue "T" and/or the enabled zone "EZ". Requiring the clinician's gaze to be directed to the target tissue "T" or the enabled zone "EZ" before enabling the function of the tool 20 provides an additional level of safety to the surgical procedure.

As detailed above, the endoscope 200 can be movable about the surgical site "S". It is contemplated that as the endoscope 200 is moved about the surgical site "S" the function of the tool 20 would be disabled until the position of the endoscope 200 is stationary. By disabling the function of the tool 20 as the endoscope 200 is moved about the surgical site "S" provides an additional level of safety to the surgical procedure.

Figure 6:
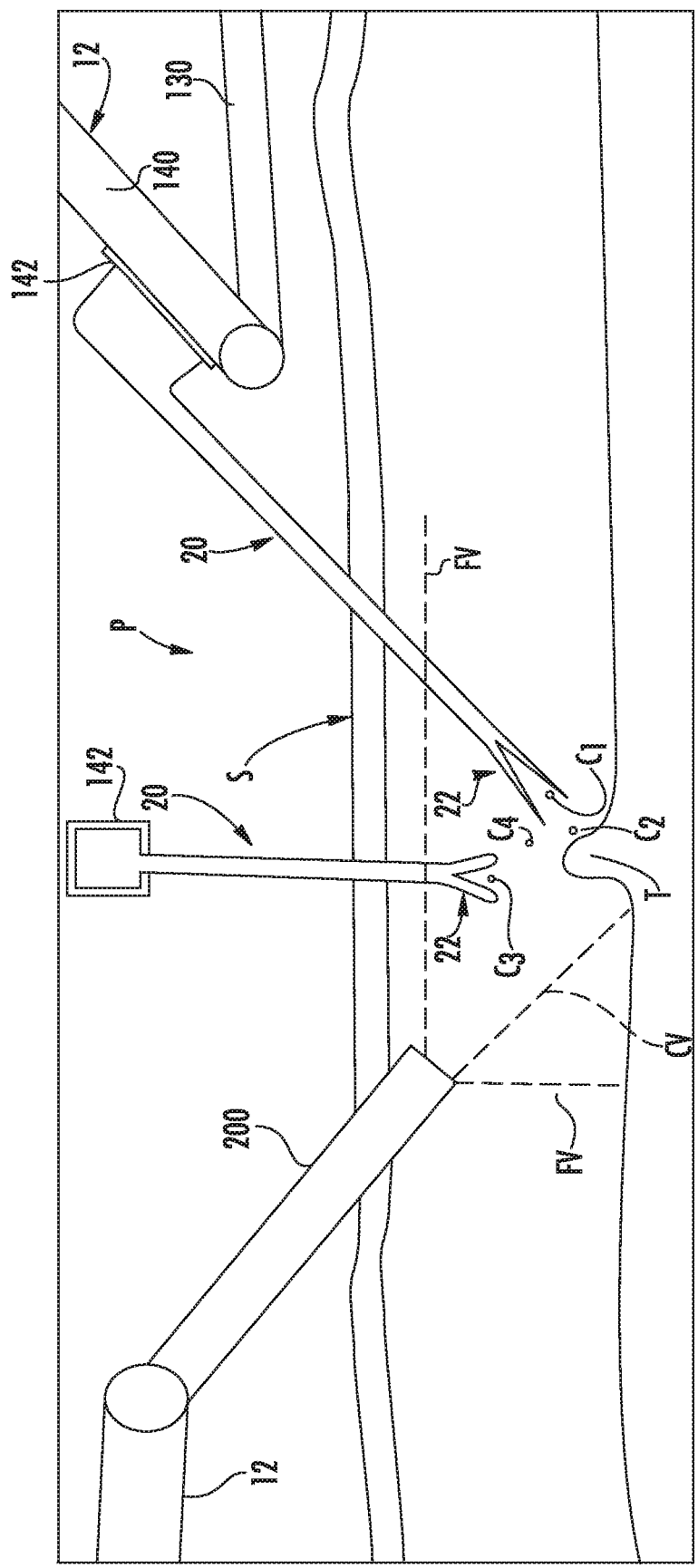
FIG. 6 is a schematic illustration of a surgical site with tools of the robotic system of FIG. 1 inserted therein illustrating centroids for directing a center of view of an imaging device.

Referring to FIG. 6, a method for changing a center of view and/or field of view of the imaging device or endoscope 200 during a surgical procedure is described utilizing the robotic surgical system 1 detailed above. During a surgical procedure the view of the surgical site "S" can track the end effector 22 of a tool 20 within the surgical site "S". By tracking the end effector 22 of the tool 20, the attention or focus of a clinician engaged with the user interface 40 can be directed to the surgical procedure and not be distracted or consumed by directing the center of view of the endoscope 200.

The endoscope 200 is disposed on an arm 12 of the robotic system 10 (FIG. 2) such that the robotic system 10 can manipulate the endoscope 200 during a surgical procedure. Initially the endoscope 200 is introduced into the surgical site "S" with a center of view of the endoscope directed towards an area of interest. The area of interest can be an entry point of the end effector 22 of the tool 20 into the surgical site "S" or can be directed to targeted tissue "T" within the surgical site "S". In addition, a field of view of the endoscope 200 can be set to encompass a large area of the surgical site "S".

With the field and center of view "CV" of the endoscope 200 set, the end effector 22 of the tool 20 is brought within a field of view "FV" the endoscope 200. The endoscope 200 is then used to determine a tool pose of the tool 20 as detailed above. From the tool pose, a centroid "$C_1$" of the end effector 22 can be determined. The center of view of the endoscope 200 is re-centered to be directed to the centroid "$C_1$" of the end effector 22 such that the centroid "$C_1$" is tracked by the endoscope 200. As used herein, it is understood that centroid may include features or the like, or locations that are mathematically computable.

During the surgical procedure it will be appreciated that the centroid "$C_1$" of the end effector 22 is moved about the surgical site "S". As the centroid "$C_1$" is moved, the center of view "CV" of the endoscope 200 re-centers to track the centroid "$C_1$" of the end effector 22. By re-centering the center of view "CV" of the endoscope 200 during the surgical procedure, the attention and focus of the clinician can be directed to the surgical procedure.

The re-centering can be done in a manner such that the center of view "CV" of the moves in a manner that does not distract a clinician viewing the display 44 (FIG. 1). The re-centering is done in a matter such that the velocity of the re-centering can be controlled to ensure a perceptually appropriate experience during re-centering of the center of view "CV". The re-centering can implement a dwell time of the centroid "$C_1$" such that the re-centering occurs in a smooth manner. The re-centering can also have a maximum velocity of the center of view "CV" of the endoscope 200. In addition, the re-centering can also shape an acceleration/deceleration of the center of view "CV" of the endoscope 200 at the start and end of movement to keep the re-centering of the center of view "CV" to be comfortable for the clinician engaging the user interface 40. Further, the re-centering may incorporate a form of hysteresis to prevent continuous chasing of the center of view "CV" to the end effector 22. For example, the re-centering may not occur until the centroid of the end effector 22, e.g., centroid "$C_1$", is offset from the center of view "CV" of the endoscope by a predefined distance, e.g., about 3 cm. It is envisioned that the re-centering can be fully automated or be selectively activated at the discretion of a clinician.

It is contemplated that, the center of view of the endoscope 200 can track a centroid "$C_2$" which is centered between the centroid "$C_1$" of the end effector 22 and the targeted tissue "T". In addition, the endoscope 200 can adjust its field of view "FV" based on the distance between the centroid "$C_1$" of the end effector 22 and the targeted tissue "T" such that as the end effector 22 approaches the targeted tissue "T", the endoscope 200 zooms in or reduces the size of the field of view "FV". In addition, as the end effector 22 moves away from the targeted tissue "T", the endoscope 200 zooms out or increased the size of the field of view "FV".

During surgical procedures with two tools 20 within the surgical site "S", the center of view "CV" of the endoscope 200 can track a centroid "$C_4$" that is a centered between the centroid "$C_1$" of a first end effector 22 and a centroid "$C_3$" of a second end effector 22. By tracking the centroid "$C_4$" with the center of view "CV" of the endoscope 200, interactions of the first and second end effectors 22 can be viewed by the clinician. In addition, the endoscope 200 can change its field of view "FV" to zoom in and out based on the distance between the centroids "$C_1$" and "$C_3$". Alternatively, the center of view "CV" of the endoscope 200 can track the centroid "$C_2$" centered between the centroid "$C_1$" of the first end effector 22 and the targeted tissue "T" and disregard the centroid "$C_3$" of the second end effector 22. It will be appreciated that a form of hysteresis may also be introduced to the tracking of the centroid "$C_4$" with the center of view "CV" of the endoscope 200.

During surgical procedures with more than two tools 20 within the surgical site "S", the center of view "CV" of the endoscope 200 can track a centroid (e.g., centroid "$C_4$") that is centered between centroids (e.g., centroids "$C_1$" and "$C_3$") of active end effectors 22 in a manner similar to that detailed above with respect to two tools 20. As the active end effectors 22 change within the surgical site "S", the center of view "CV" of the endoscope 200 re-centers on a centroid between the active end effectors 22.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method of controlling a function of a tool of a surgical system, the method comprising:
   capturing images of a surgical site with an imaging device;
   determining a distance of the tool within the surgical site relative to targeted tissue;
   enabling activation of a function of the tool when the tool is within a predetermined distance from the targeted tissue;
   activating the function of the tool to manipulate tissue with the tool in response to a control signal; and
   disabling activation of the function of the tool when the tool is beyond the predetermined distance from the targeted tissue.

2. The method according to claim 1, wherein enabling activation of the function of the tool includes providing visual indicia to a clinician engaged with the surgical system that the function is enabled.

3. The method according to claim 2, wherein providing visual indicia includes changing a color of a border of a display of the surgical system.

4. The method according to claim 1, wherein disabling activation of the function includes providing visual indicia to a clinician engaged with the surgical system that the function is disabled.

5. The method according to claim 4, wherein providing visual indicia includes changing a color of a border of a display of the surgical system.

6. The method according to claim 1, further comprising the surgical system completing an automated task within the surgical site with the tool when the tool is within the predetermined distance from the targeted tissue.

7. The method according to claim 6, wherein completing the automated task includes suturing the targeted tissue when the tool is within the predetermined distance from the targeted tissue.

8. The method according to claim 1, further comprising verifying that a gaze of a clinician interfacing with the surgical system is directed to an enabled zone on a display of the surgical system before enabling activation of the function of the tool.

9. The method according to claim 1, wherein activating the function of the tool to manipulate tissue with the tool includes at least one of clamping tissue with the tool, delivering electrosurgical energy to tissue with the tool, stapling tissue with the tool, suturing tissue with the tool, or advancing a cutting edge of the tool through tissue.

10. A surgical system comprising:
    an imaging device configured to capture images of a surgical site;
    a tool having a function, the function configured to manipulate tissue in response to a control signal; and
    a processing unit in communication with the imaging device and the tool, the processing unit configured to:

determine a distance of the tool relative to targeted tissue from the captured images;
enable activation of the function of the tool when the tool is positioned within a predetermined distance of the targeted tissue; and
prevent activation of the function of the tool when the tool is positioned beyond the predetermined distance from the targeted tissue.

11. The surgical system according to claim 10, further comprising a display configured to provide a representation of the surgical site.

12. The surgical system according to claim 11, wherein the processing unit is configured to provide a representation of an enablement zone defined by the predetermined distance within the representation of the surgical site.

13. The surgical system according to claim 11, wherein the processing unit is configured to provide visual indicia on the display when the function of the tool is enabled.

14. The surgical system according to claim 13, wherein the display is configured to change a color of a border of the display when the function of the tool is enabled.

15. The surgical system according to claim 10, further comprising a display configured to provide a representation of the surgical site, the processing unit configured to verify that a gaze of a clinician is directed to the display before enabling activation of the function of the tool.

16. The surgical system according to claim 10, wherein the processing unit is configured to complete an automated task when the tool is within the predetermined distance of the targeted tissue.

* * * * *